(12) United States Patent
Paolini et al.

(10) Patent No.: US 8,684,959 B2
(45) Date of Patent: Apr. 1, 2014

(54) EXTRACORPOREAL BLOOD TREATMENT APPARATUS

(75) Inventors: Francesco Paolini, Genaceto (IT); Francesco Fontanazzi, Modena (IT); Fabio Grandi, Forli (IT)

(73) Assignee: Gambro Lundia AB, Lund (SE)

( * ) Notice: Subject to any disclaimer, the term of this patent is extended or adjusted under 35 U.S.C. 154(b) by 219 days.

(21) Appl. No.: 13/003,126

(22) PCT Filed: Jul. 3, 2009

(86) PCT No.: PCT/IB2009/006162
§ 371 (c)(1),
(2), (4) Date: Jan. 7, 2011

(87) PCT Pub. No.: WO2010/004400
PCT Pub. Date: Jan. 14, 2010

(65) Prior Publication Data
US 2011/0118647 A1      May 19, 2011

(30) Foreign Application Priority Data
Jul. 9, 2008   (IT) .............................. MI2008A1247

(51) Int. Cl.
*A61M 37/00*        (2006.01)

(52) U.S. Cl.
USPC ....... 604/6.09; 604/4.01; 604/5.01; 604/5.04; 604/6.01; 604/6.06

(58) Field of Classification Search
CPC ......................... A61M 1/16; A61M 2001/1647
USPC ............ 604/4.01, 5.01, 5.04, 6.01, 6.06, 6.09
See application file for complete search history.

(56) References Cited

U.S. PATENT DOCUMENTS

| 4,324,663 A | * | 4/1982 | Hirel et al. .................... 210/646 |
| 4,469,593 A | | 9/1984 | Ishihara et al. |

(Continued)

FOREIGN PATENT DOCUMENTS

| CA | 1 121 738 A1 | 4/1982 |
| EP | 0 186 973 A2 | 7/1986 |

(Continued)

OTHER PUBLICATIONS

Casagrande et al. ("A new method to evaluate patient characteristic response to ultrafiltration during hemodialysis," The International Journal of Artificial Organs, vol. 30, No. 5, 2007, pp. 1-8).*

(Continued)

*Primary Examiner* — Philip R Wiest
*Assistant Examiner* — Ariana Zimbouski
(74) *Attorney, Agent, or Firm* — Pearne & Gordon LLP

(57) ABSTRACT

An extracorporeal blood treatment apparatus comprises a sensor (10) for emitting a signal indicating a change of hematic volume of an individual (7) subjected to a treatment and a weight loss system for actuating the individual's weight loss. A control unit (20) receives an effective weight value of the individual and a desired weight loss value and from these values determines a desired value of a change in hematic volume at end of treatment. The weight loss system is controlled on a basis of the hematic volume change signal and the desired value of the hematic volume change. The apparatus enables automatic control of a dialysis operation while preventing some complications arising from hypotension.

13 Claims, 1 Drawing Sheet

(56) References Cited

U.S. PATENT DOCUMENTS

| | | | | |
|---|---|---|---|---|
| 4,629,015 | A | * | 12/1986 | Fried et al. .................. 177/25.19 |
| 5,938,938 | A | * | 8/1999 | Bosetto et al. ................. 210/739 |
| 7,131,956 | B1 | * | 11/2006 | Pirazzoli et al. ............. 604/6.09 |
| 8,075,509 | B2 | * | 12/2011 | Molducci et al. ............ 604/6.09 |
| 8,496,807 | B2 | * | 7/2013 | Mori et al. ...................... 210/86 |

FOREIGN PATENT DOCUMENTS

| | | |
|---|---|---|
| EP | 1 872 811 A1 | 1/2008 |
| GB | 2 052 303 A | 1/1981 |
| IT | 1 105 139 B | 10/1985 |
| IT | 1 252 601 B | 6/1995 |
| IT | 1 276 468 B1 | 10/1997 |
| WO | 93/00938 A1 | 1/1993 |
| WO | 97/02057 A1 | 1/1997 |

OTHER PUBLICATIONS

Winkler Roland E. et al., "Blood vol. Monitoring", Basic Research to Clinical Trials. Contrib Nephrol. Basel, Karger, 2008, vol. 161, pp. 119-124.

Von Sarti E. et al., "Optimal Hemodialysis Programming by a Mathematical Modell", 10th Annual Conference of the IEEE EMBS, 1988, 8 pages.

Casagrande G. et al., "A new method to evaluate patient characteristic response to ultrafiltration during hemodialylsis", The International Journal of Artificial Organs, vol. 30, No. 5, 2007, pp. 1-8.

Lamberti C. et al., "A digital computer model for optimal programming of hemodialytic treatment", The International Journal of Artificial Organs, vol. 11, No. 4, 1988, pp. 235-242.

Schroeder Kevin L. et al., "Continuous haematocrit monitoring during intradialytic hypotension: precipitous decline in plasma refill rates", Nephrology Dialysis Transplantation (2004), vol. 19, No. 3, pp. 652-656.

Santoro Antonio et al.: "Blood Volume Regulation During Hemodialysis", American Journal of Kidney Diseases, vol. 32, No. 5 (November); 1998; pp. 739-748.

Schönweiss, Gunther, "Dialysefibel 3, Band 2", Abakiss Verlagsgesellschaft mbH, paragraph 9.6 Hämodialysegerate—Wasserseite, p. 613, 2006, 4 pages.

Wikipedia, "Dialyse", in Internet at http://de.wikipedia.org/wiki/Dialyse, found on Sep. 12, 2012, 6 pages.

* cited by examiner

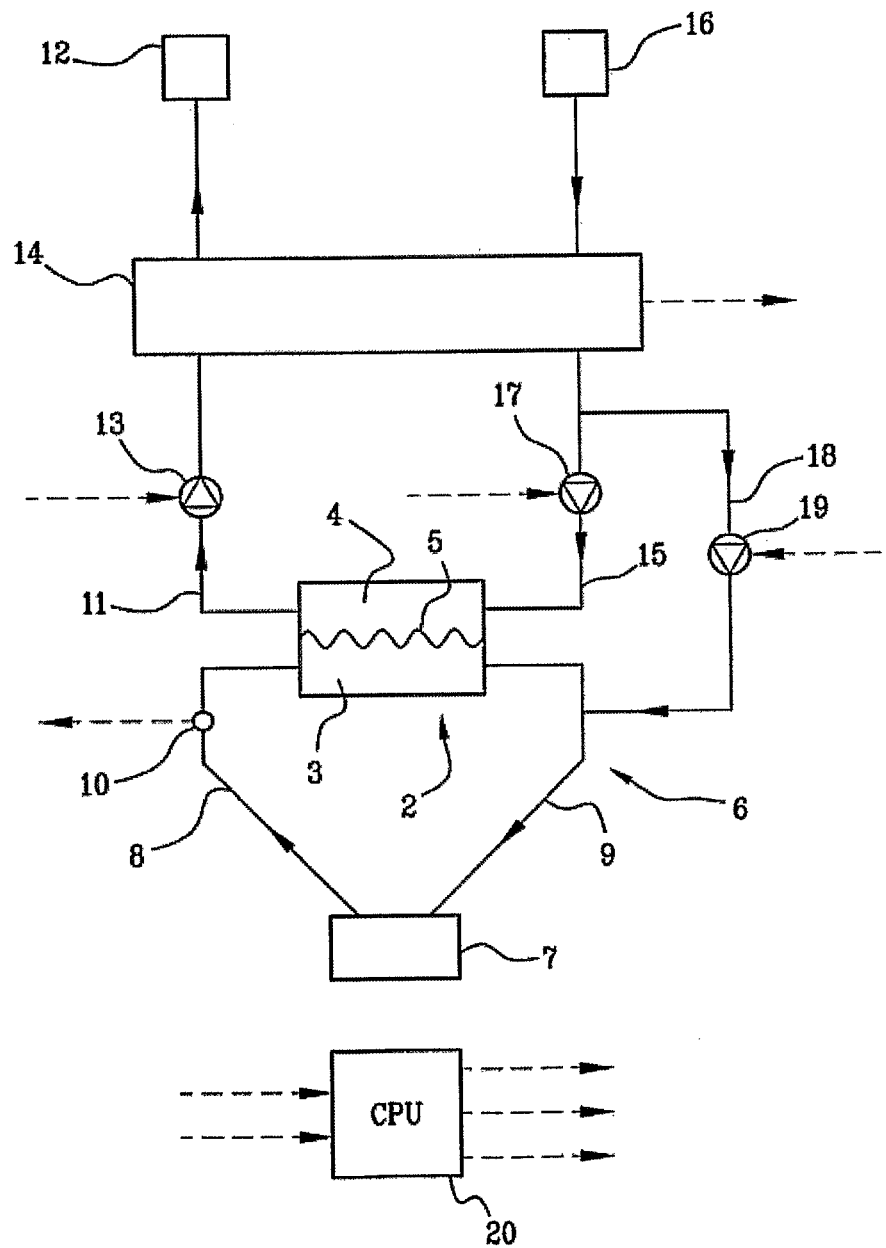

EXTRACORPOREAL BLOOD TREATMENT APPARATUS

The invention relates to an apparatus for extracorporeal blood treatment. Specifically, though not exclusively, the invention can be usefully applied in the treatment of kidney failure.

Automatic control of progress of a dialysis treatment is known, especially control of the amount of patient weight loss and the conductivity of the dialysis fluid, taking account in real-time of the physiological response of the patient to the treatment, especially monitoring the change in the hematic volume of the patient, with the aim of improving the well-being of the patient her or himself, especially by preventing any hypotensive phenomena during treatment.

U.S. Pat. No. 4,449,593 illustrates a dialysis treatment control system in which if the hematocrit value measured in the extracorporeal blood during the treatment is less than or greater than a desired and stored value, an ultrafiltration pump velocity is gradually increased or respectively reduced.

Italian patent IT 1252601 describes an automatic dialysis system in which desired time-variable values of the relative change in hematic volume are stored, and effective values of the relative change in hematic volume are measured during treatment, leading to a calculation of the patient parameter values (corresponding to the coefficients of a predetermined mathematical model having in entry one or more machine data readings and in exit a relative change in hematic volume) according to the real response of the patient to the treatment; then a calculation is made of the values of the machine data readings (weight loss speed, the osmolarity of the dialysis solution and the infusion velocity) according to the calculated patient parameters.

Italian patent IT 1276468 describes an automatic dialysis system in which desired values and real values are acquired of the relative change in hematic volume and patient weight loss; during treatment the real values of the weight loss velocity and the conductivity of the dialysis liquid are acquired, and permitted values are also memorised over a time period of the relative hematic volume change, the accumulated weight loss, the velocity of the weight loss and the conductivity of the dialysis liquid, and finally a calculation is made and used in the control of the operating values of the velocity of the weight loss and conductivity of the dialysis liquid.

An article entitled "A new method to evacuate patient characteristic response to ultrafiltration during hemodialysis", which appeared in "The International Journal of Artificial Organs", Vol. 30, no. 5, 2007, teaches that the parameter termed "Plasma Refilling Index" (PRI), defined by the relation between total body water of an individual and her or his hematic volume, provides useful indications in understanding the response of a patient subjected to dialysis, in particular his behaviour concerning vascular "refilling", i.e. the quantity of liquid which is displaced from the interstitial space of the patient's body to the intravascular space thereof.

SUMMARY OF THE INVENTION

An aim of the present invention is to provide an automatic control system of an extracorporeal blood treatment which is able efficiently to adapt to the various characteristics and needs of each patient in order to guarantee maximum well-being of the patient during treatment.

An advantage of the invention is that it provides a control system able to prevent some complications during the course of treatment, such as for example collapse, cramp, vomiting, headache, etc.

A further advantage is that it makes available a control system which can be set by an operator simply, rapidly and reliably.

A further advantage is that it gives rise to a control system which takes account with particular precision of the effective physiological situation of the patient and which can thus adapt remarkably effectively to the individual reactions of the patient during the course of the treatment.

Further characteristics and advantages of the present invention will better emerge from the detailed description that follows, of at least an embodiment of the invention, illustrated by way of non-limiting example in the accompanying figures of the drawings.

BRIEF DESCRIPTION OF THE DRAWING

The description will be made herein below with reference to the accompanying figure of the drawings, which is provided by way of non-limiting example.

FIG. 1 is a diagram of an extracorporeal blood apparatus in an embodiment of the present invention.

DETAILED DESCRIPTION

With reference to FIG. 1, 1 denotes in its entirety an extracorporeal blood treatment apparatus, which in the specific case comprises a hemodiafiltration apparatus. The extracorporeal blood treatment apparatus can comprise any one of the hemodialysis or hemo(dia)filtration apparatus of the known art.

2 denotes a blood treatment device (hemodialyser) having a blood chamber 3 and a fluid chamber 4 which are separated from one another by a semipermeable membrane 5. 6 denotes an extracorporeal blood circuit connected to the blood chamber 3 in order to transport blood from an individual 7 to the blood chamber 3 and to return the blood from the blood chamber 3 to the individual 7. The blood circuit 6 comprises a removal line 8 (arterial line) and a return line 9 (venous line). The removal line 8 and the return line 9 can comprise any one of the arterial and venous lines known in the prior art and used in a hemodialysis or hemo(dia)filtration apparatus. In particular the removal line 8 and the return line 9 can be provided with and/or connected to various sensors and actuators of known type (for example pressure sensors, blood presence sensors or patient sensors, liquid level sensors, air presence sensors, blood transport pumps, infusion liquid transport pumps, automatic check valves, liquid level regulation devices, etc.) for control and monitoring of the circuit, and to various devices of known type (gas-liquid separating devices, access sites for removal/injection, manual clamps, service lines, etc.) for performing various operations on the circuit. 10 denotes in particular a sensor predisposed in the extracorporeal blood circuit (in the specific case in the removal line 8) for emitting at least a signal indicating the change in hematic volume of the individual subjected to extracorporeal blood treatment. The sensor 8, of known type, can emit for example an optical or acoustic signal. In the specific case the hematic volume 8 change sensor 8 comprises a hematocrit sensor. The signals emitted by the hematocrit sensor during the treatment are used in a known way for determining the change in hematic volume of the individual 7.

The apparatus 1 comprises a weight loss system for actuating the weight loss of the individual during the extracorporeal blood treatment. In the specific case the weight loss system comprises a discharge line 11 connected to an outlet of the fluid chamber 4 for removing a discharge liquid from the chamber and sending it to a drainage 12. 13 denotes a discharge pump for moving the discharge liquid. 14 denotes a sensor configured for emitting at least a signal indicating the weight loss of the individual subjected to the extracorporeal blood treatment. In the specific case the sensor 14 comprises any one of the known-type sensor means used for detecting the weight loss of a patient in an ultrafiltration, a hemodialysis or a hemodiafiltration apparatus. In the specific case, in which the apparatus 1 is a hemodiafiltration apparatus, the sensor 14 can comprise, for example, the following systems of known type: a system of two flow-meters (one upstream and one downstream of the hemodiafilter), or a differential flow-meter, or a system of balances, or a system of control of the filling to predetermined volumes, or an ultrafiltration flow-rate sensor in the ambit of a fluid balancing system with variable-volume chambers, or other systems of known type.

The hemodiafiltration apparatus comprises a supply system for supplying a treatment fluid of a predetermined composition to the fluid chamber 4. The supply system can comprise any one of the supply systems of known type used for supplying a dialysis fluid and/or a substituting fluid in a hemodialysis apparatus or hemo(dia)filtration apparatus (for example of a type with in-line preparation of the treatment fluid starting from water and concentrates or of the type which is sourced from a batch). In the specific case the supply system comprises a supply line 15 connected to an inlet of the fluid chamber 4, a source 16 of the treatment fluid (batch-type or in-line preparation type) and a supply pump 17. The sensor 14 in this case will be connected to the supply line 15 in order to take account, in determining the weight loss of the individual, also of the treatment fluid flow, in particular the dialysis fluid which enters the fluid chamber 4 and/or the substitution fluid infused into the extracorporeal circuit 6. In the specific case the source 16 comprises a device for in-line preparation of a treatment fluid with a predetermined concentration. The preparation device can comprise any one of the devices of known type used for this aim 1n a hemodialysis or hemo(dia)filtration machine. In particular the preparation device can prepare the treatment fluid starting from water and concentrates by means of the use of one or more electrical conductivity sensors for determining, in a known way, the composition of the prepared fluid. The structure and functioning of the treatment fluid preparation device is known and will therefore not be further explained herein.

In use, the hemodiafiltration apparatus operates, in a known way, to effect a predetermined weight loss in the individual, giving rise to an ultrafiltration device for ultrafiltering liquid from the blood chamber 3 to the fluid chamber 4 through the semipermeable membrane 5. In particular the ultrafiltration is performed thanks to the pressure difference on the two sides of the membrane 5 (transmembrane pressure) and the consequent convective transport of liquid generated by the discharge pump 13 which enables a pressure to be obtained in the fluid chamber 4 that is lower than the pressure in the blood chamber 3. The ultrafiltration means are substantially of known type and thus do not require further explanation. It is also possible to use any other known method of ultrafiltration.

The hemodiafiltration apparatus comprises an infusion device for infusing liquid into the extracorporeal circuit. In the specific case the infusion device comprises an infusion line 18 and an infusion pump 19 for the movement of the infusion fluid. In the specific case the infusion line 18 is connected in a branch relation with the supply line 15 via a branching point arranged downstream of the sensor 14. The infusion line can be connected to an infusion fluid batch source. In the specific case the infusion line 18 is connected to the return line 9 (post-dilution), even though it would be possible to have, additionally or alternatively to the line 18, an infusion line, not illustrated, connected to the removal line 8 (pre-dilution).

The extracorporeal blood treatment apparatus comprises a control unit 20 configured to receive the relative blood and weight volume variation signals during the extracorporeal blood treatment.

The control unit is configured to receive an effective weight value for the patient, a desired weight loss value for the patient, and is configured to determine at least a desired value of an individual's parameter (in particular the change in hematic volume desired at the end of the treatment) on the basis of the effective weight value and the desired weight loss, and is also configured to control the weight loss system (in particular ultrafiltration and/or infusion and/or supply of dialysis fluid) from the above signal of hematic volume change and the desired value of a parameter of the individual.

The control unit is configured to determine a plurality of desired values of the individual's parameter according to the treatment time (for example a desired profile of the hematic volume change during the course of treatment) on the basis of the desired value of the individual's parameter, which in particular might comprise an objective value of the individual's parameter (for example the change in the individual's hematic volume) which it is desired to obtain at the end of the treatment.

The above-mentioned operation of determining at least a desired value of an individual's parameter might comprise the sub-operations of receiving (for example by entering a value via a user interface) a desired value of a second parameter of an individual (the second parameter being, for example the refilling index or another parameter which is a function of the individual's parameter, the above-cited effect weight value and the desired weight-loss value) and calculating the desired value of the individual's parameter (change in hematic volume) on the basis of the previously-received desired value of the second parameter of the individual (refilling index).

The second parameter of the individual can comprise a relation between the relative change in hematic volume and the relative weight loss, where the relative weight loss comprises a relation between a desired weight loss and an effective weight of the patient. In particular, as mentioned, the second parameter of the individual might comprise a refilling index RI as follows:

$$RI = \frac{\Delta BV\ \%}{WL\ \%}$$

where $\Delta BV\%$ is the relative change in hematic volume, i.e. the change in hematic volume in relation to the total hematic volume, and $WL\%$ is the relative weight loss, i.e. the weight loss in relation to the total weight of the individual or the weight of the bodily water of the individual.

The control unit can further be configured to receive a minimum threshold value and/or a maximum threshold value of acceptability for the second parameter of the individual. In the specific case in which the second parameter of the individual is the refilling index, the minimum threshold value might be comprised between 0.5 and 1.1, while the maximum threshold value might be between 1.2 and 2.5.

The control unit can be further configured to receive a range of acceptable values for the second parameter of the individual. In the specific case in which the second parameter of the individual is the refilling index, the range of acceptable values might be from 0.5 to 2.5, or from 0.5 to 2.0, or from 0.7 to 1.5, or from 0.75 to 1.3.

The above effective weight value of the individual might comprise a value selected from among the total body weight of the individual before or after the treatment and the weight of the bodily water of the individual before or after the treatment.

The control unit might also be configured for controlling the ultrafiltration device on the basis of the signal of change in hematic volume and the desired value of a parameter of the individual. The control unit might also be configured for controlling the infusion device on the basis of the hematic volume change signal and the desired value of a parameter of the individual. Further, the control unit might also be configured for controlling the treatment fluid supply system (in particular the composition of the fluid via concentration/conductivity measurements) on the basis of the above-mentioned hematic volume change signal and the desired value of a parameter of the individual.

The control unit might operate the automatic control of the weight loss (plasmatic ultrafiltration and/or infusion fluid supply/substitution and/or supply of dialysis fluid) as described in Italian patents IT 1252601 and IT 1276468, on the basis of the detection of the hematic volume change, the weight loss and the conductivity of the dialysate, taking however into account the fact that in this case the objective value of the hematic volume change (particularly at the end of treatment) is obtained starting from the effective value of the patient's weight (wet/dry, before/after the treatment). In this case in particular the desired profile for the hematic volume change according to treatment time is obtained as described in the above-mentioned patents IT 1252601 and IT 1276468, but using as a reference point the objective value of the hematic volume change (especially the value at end of treatment) obtained starting from the effective weight value of the patient.

EXAMPLE

Let us suppose that for a certain patient it has been ascertained that on the basis of dialytic treatments undertaken previously and the consequent physiological reactions, an optimal value for the refilling index is 1.0, which is therefore used as a setting value:

$$RI=1.0$$

This value is entered by the operator as a setting value for the treatment, using the user interface of the apparatus.

The operator further enters a weight value for the patient, for example by using the user interface of the apparatus. This value can be the weight of the patient before treatment (known as the wet weight) or the patient's weight after the treatment (known as the dry weight), or it can be the weight of the patient's bodily water (before or after the treatment). The weight of the bodily water is calculable, as is known, as a function of the total weight of the patient, for example via a proportionality factor (sometimes known as the bodily weight distribution volume) which is normally considered to be between 50% and 60%, for example 55%. Thus, supposing for example that the dry weight of the patient (at end of treatment) is 80 Kg, the weight of the bodily water at end of treatment can be calculated at 80*0.55=44 Kg.

$$BWW=44\ Kg$$

The operator further enters the total body weight loss of the patient (for example 4.5 Kg).

$$TWL=4.5\ Kg$$

This value too is entered as a setting value via the apparatus user interface. The control unit can thus calculate the percentage weight loss, i.e. the total weight loss normalised on the basis of the total weight (of the bodily water):

$$WL\ \%=TWL/BWW$$

In the specific case $$WL\ \%=4.5/44\approx 0.10227\approx 10.2\%$$

The percentage weight loss can also be normalised on the basis of the total weight of the patient before or after treatment or the weight of the bodily water before treatment.

The percentage variation of the hematic volume (i.e. the variation in hematic volume normalised on the basis of the initial hematic volume) which it is desired to obtain at the end of treatment is thus calculated on the basis of the percentage weight loss and the preset value of the refilling index according to the following formula:

$$\Delta BV\ \%=RI*WL\ \%$$

In the specific case $$\Delta BV\ \%=1.0*10.2=10.2\%$$

This value for $\Delta BV\ \%$ is a desired value, i.e. the value of the percentage variation of the hematic volume which it is desired to obtain at the end of treatment.

Starting from the desired value $\Delta BV\ \%$ a desired profile is calculated for the percentage variation of the hematic volume during the course of the treatment. It is evident that the initial value of $\Delta BV\ \%$ will be 0. This calculation of the profile can be performed using known methods, such as for example the one used in the Hemocontrol® control system of the Integra® dialysis machine. The determination of the desired profile for a certain patient can be performed, for example, by analysing the effective profile for that patient for a certain number of treatments.

Once the desired profile of the relative hematic volume change $\Delta BV\ \%$ has been defined and stored by the control unit, the treatment can begin and proceed in a known way so that the relative variation in hematic volume which is effectively measured for the patient during the course of treatment follows the desired profile, at least within predetermined upper and lower limits. The control system for reaching this objective can be, as mentioned, of known type, for example a control system operating on the amount of weight loss of the patient and/or the conductivity of the dialysis fluid and/or the amount of the infusion liquid. The control system can comprise, for example, the system described in Italian patent IT 1252601 (which is incorporated herein for the sake of reference) or the Hemocontrol® used in Integra® dialysis machines.

The individual's weight can comprise, for example, the total body weight or the bodily water weight or another weight. The individual's weight can comprise a weight considered wet or dry, or in another way. The control unit can be configured to receive the effective value of the individual's weight which will be used as input directly from outside. The determination of the weight can also be performed (possibly also by the control unit of the treatment apparatus) by any one of the formulas of known type usable for this purpose, such as for example the formulas for the determination of the total bodily water volume (Watson's formula, Hume-Weyer's formula, Mellits-Cheek's formula, etc.). The control unit, for example, can receive in input data relating to the patient to be subjected to the treatment (for example sex, age, height, total weight etc) and this data, via the use of one of the stored known formulas, can be configured to determine in outlet the total bodily water volume. It is also possible for the control unit to be configured to determine the weight of the individual in real-time, for example in a period of time at the start of treatment, on the basis of reading made by the sensors of the treatment apparatus or by external sensors applied to the individual and connected to the control unit of the apparatus. It is therefore possible for the individual's weight value not necessarily to be introduced as input from the outside (for example by an operator or by means of an identification system of the individual) but to be calculated directly in-line, in particular with the individual connected to the treatment apparatus, using a mathematical model and values measured in-line.

The invention claimed is:

1. An extracorporeal blood treatment apparatus, comprising:
    a blood treatment device having a blood chamber and a fluid chamber separated from one another by a semipermeable membrane;
    an extracorporeal blood circuit connected to the blood chamber for transporting blood from an individual to the blood chamber and for returning the blood from the blood chamber to the individual;
    a sensor predisposed in the extracorporeal blood circuit for emitting at least a signal indicating a variation in hematic volume of the individual subjected to extracorporeal blood treatment;
    a weight loss system for actuating an individual's weight loss during the extracorporeal blood treatment;
    a control unit configured for performing following operations:
    receiving an effective weight value of the individual;
    receiving a desired weight loss value of the individual;
    determining at least a desired value of a hematic volume change of the individual on a basis of the effective weight value and the desired weight loss value, wherein the operation of determining at least a desired value of a hematic volume change comprises sub-operations of:
        receiving a desired value of a second parameter of the individual, wherein said second parameter is a Refilling Index;
        calculating a desired value of the individual's parameter on a basis of the desired value of the individual's second parameter, the effective weight value and the desired value of the weight loss by calculating a relative hematic volume change on a basis of the desired value of the individual using formula:

$$\Delta BV\% = RI * WL\%$$

where $\Delta BV\%$ is the variation in relative hematic volume, i.e. the variation of hematic volume in relation to the total hematic volume, RI is the desired value of the individual's
    second parameter and WL% is the relative weight loss where the relative weight loss is calculated on a basis of a relation between the desired weight loss and the effective weight of the patient;
    controlling the weight loss system on a basis of the signal of hematic volume change and the desired value of a parameter of the individual.

2. The apparatus of claim 1, wherein the control unit is configured for determining a plurality of desired values of the individual's parameter according to a treatment time on a basis of the at least a desired value of the individual's parameter.

3. The apparatus of claim 1, wherein the desired value of an individual's parameter comprises an objective value which it is desired to obtain at end of treatment.

4. The apparatus of claim 1, wherein the control unit is configured to receive a minimum and a maximum threshold value of acceptability for the individual's second parameter.

5. The apparatus of claim 1, wherein the control unit is configured for receiving a range of acceptability for the individual's second parameter.

6. The apparatus of claim 5, wherein the range of acceptability is comprised between 0.5 and 2.0.

7. The apparatus of claim 1, wherein the effective weight value of the individual comprises a value selected from between the total body weight of the individual before or after the treatment and the weight of the individual's bodily water before or after the treatment.

8. The apparatus of claim 1, wherein the weight loss system comprises an ultrafiltration device for liquid ultra-filtration from the blood chamber to the fluid chamber through the semipermeable membrane, the control unit being configured for controlling the ultrafiltration device on a basis of the hematic volume change signal and the desired value of a parameter of the individual.

9. The apparatus of claim 1, wherein the weight loss system comprises an infusion device for infusing a liquid into the extracorporeal circuit, the control unit being configured for controlling the infusion device on a basis of the hematic volume change signal and the desired value of a parameter of the individual.

10. The apparatus of claim 1, comprising a supply system for supplying a treatment fluid of a predetermined composition to the fluid chamber, the control unit being configured for controlling the supply system on a basis of the hematic volume change signal and the desired value of a parameter of the individual.

11. An extracorporeal blood treatment apparatus, comprising:
    a blood treatment device having a blood chamber and a fluid chamber separated from one another by a semipermeable membrane;
    an extracorporeal blood circuit connected to the blood chamber for transporting blood from an individual to the blood chamber and for returning the blood from the blood chamber to the individual;
    a sensor predisposed in the extracorporeal blood circuit for emitting at least a signal indicating a variation in hematic volume of the individual subjected to extracorporeal blood treatment;
    a weight loss system for actuating an individual's weight loss during the extracorporeal blood treatment;
    a control unit configured for performing following operations:
    receiving an effective weight value of the individual;
    receiving a desired weight loss value of the individual;
    determining at least a desired value of a hematic volume change of the individual on a basis of the effective weight value and the desired weight loss value, wherein the operation of determining at least a desired value of a hematic volume change comprises sub-operations of:
        receiving a desired value of a second parameter of the individual, wherein said desired value of said second parameter is the optimal value of a Refilling Index for that individual;
        calculating a desired value of the individual's parameter on a basis of the desired value of the individual's second parameter, the effective weight value and the desired value of the weight loss by calculating a relative hematic volume change on a basis of the desired value of the individual using formula:

$$\Delta BV \% = RI * WL \%$$

where $\Delta BV \%$ is the variation in relative hematic volume, i.e. the variation of hematic volume in relation to the total hematic volume, RI is the desired value of the individual's second parameter and WL % is the relative weight loss where the relative weight loss is calculated on a basis of a relation between the desired weight loss and the effective weight of the patient;

controlling the weight loss system on a basis of the signal of hematic volume change and the desired value of a parameter of the individual.

12. The apparatus of claim 11, wherein the optimal value of the Refilling Index for that individual is ascertained on the basis of dialytic treatments undertaken previously.

13. The apparatus of claim 11, where $\Delta BV \%$ is the variation in relative hematic volume at the end of the treatment and wherein a desired profile for the percentage variation of the hematic volume during the course of the treatment is calculated.

* * * * *

UNITED STATES PATENT AND TRADEMARK OFFICE
CERTIFICATE OF CORRECTION

PATENT NO. : 8,684,959 B2
APPLICATION NO. : 13/003126
DATED : April 1, 2014
INVENTOR(S) : Paolini et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 220 days.

Signed and Sealed this
Twenty-ninth Day of September, 2015

Michelle K. Lee
*Director of the United States Patent and Trademark Office*